(12) United States Patent
Kim et al.

(10) Patent No.: US 9,409,923 B2
(45) Date of Patent: Aug. 9, 2016

(54) DRUG-FLUOROPHORE COMPLEX FOR SPECIFIC DETECTION OF TUMOR CELLS

(71) Applicant: KOREA INSTITUTE OF SCIENCE AND TECHNOLOGY, Seoul (KR)

(72) Inventors: Kwang Meyung Kim, Seoul (KR); Ick Chan Kwon, Seoul (KR); Sang Yoon Kim, Seoul (KR); Ju Hee Ryu, Seoul (KR); Eun Sung Jun, Daegu (KR); In San Kim, Daegu (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 124 days.

(21) Appl. No.: 13/936,768

(22) Filed: Jul. 8, 2013

(65) Prior Publication Data
US 2014/0288300 A1   Sep. 25, 2014

(30) Foreign Application Priority Data

Mar. 20, 2013   (KR) .................. 10-2013-0029745

(51) Int. Cl.
| | |
|---|---|
| *C07D 499/78* | (2006.01) |
| *C07D 209/62* | (2006.01) |
| *C07D 409/14* | (2006.01) |
| *C07D 498/08* | (2006.01) |

(52) U.S. Cl.
CPC ............ *C07D 499/78* (2013.01); *C07D 209/62* (2013.01); *C07D 409/14* (2013.01); *C07D 498/08* (2013.01)

(58) Field of Classification Search
CPC .. C07D 209/62; C07D 409/14; C07D 498/08; C07D 499/78
See application file for complete search history.

(56) References Cited

U.S. PATENT DOCUMENTS

2007/0212305 A1* 9/2007 Klaveness et al. ......... 424/9.341

OTHER PUBLICATIONS

Greenspan et al. "Ibuprofen Inhibits Activation of Nuclear β-Catenin in Human Colon Adenomas and Induces the Phosphorylation of GSK-3β" Cancer Prevention Research, 2011, vol. 4, pp. 161-171.*
Stummer, Walter et al., "Fluorescence-guided surgery with 5-aminolevulinic acid for resection of malignant glioma: randomised controlled multicentre phase III trial," The Lancet Oncology, vol. 7, May 2006, pp. 392-401.
Kirsch, David G. et al., "A spatially and temporally restricted mouse model of soft tissue sarcoma," Nature Medicine, Nature Publishing Group, vol. 13, No. 8, Published Online: Aug. 5, 2007, pp. 992-997.
Luker, Gary et al., Optical Imaging: Current Applications and Future Directions, The Journal of Nuclear Medicine, vol. 49, No. 1, Jan. 2008, pp. 1-4.
Sevick-Muraca, Eva et al., "Imaging of Lymph Flow in Breast Cancer Patients after Microdose Administration of a Near-Infrared Fluorophore: Feasibility Study," Radiology, Institute of Health Public Access, Mar. 2008, pp. 734-741.
von Burstin, Johannes et al., "Highly sensitive detection of early-stage pancreatic cancer by multimodal near-infrared molecular imaging in living mice," International Union Against Cancer, No. 123, 2008, pp. 2138-2147.
Tagaya, Nobumi et al., "Intraoperative identification of sentinel lymph nodes by near-infrared fluorescence imaging in patients with breast cancer," The American Journal of Surgery, No. 195, 2008, pp. 850-853.
Tromberg, Bruce J. et al., "Assessing the future of diffuse optical imaging technologies for breast cancer management," Medical Physics, vol. 35, No. 6, Jun. 2008, pp. 2443-2451.
Troyan, Susan L. et al., "The FLARE™ Intraoperative Near-Infrared Fluorescence Imaging System: A First-in-Human Clinical Trial in Breast Cancer Sentinel Lymph Node Mapping," Ann Surg Oncol., National Institute of Health Public Access, Oct. 1, 2010, pp. 1-17.

* cited by examiner

Primary Examiner — Joseph Kosack
(74) Attorney, Agent, or Firm — Goldilocks Zone IP Law

(57) ABSTRACT

Disclosed is a drug-fluorophore complex for specific detection of tumor cells. Specifically, the drug-fluorophore complex includes a tumor cell-targeting drug penetrating tumor cells and non-tumor cells at different rates or levels, and a fluorescent substance chemically bonded to the tumor cell-targeting drug. The drug-fluorophore complex enables specific imaging of tumor cells only with high accuracy in a very simple manner without causing cytotoxicity.

3 Claims, 13 Drawing Sheets

DRUG-FLUOROPHORE COMPLEX FOR SPECIFIC DETECTION OF TUMOR CELLS

CROSS-REFERENCE TO RELATED APPLICATIONS

This application claims priority under 35 U.S.C. §119 to Korean Patent Application No. 10-2013-0029745 filed on Mar. 20, 2013 in the Korean Intellectual Property Office, the disclosure of which is incorporated herein by reference in its entirety.

BACKGROUND OF THE INVENTION

1. Field of the Invention

The present invention relates to a drug-fluorophore complex for specific imaging of tumor cells only. More specifically, the present invention relates to a drug-fluorophore complex that can be used for the diagnosis of tumors during endoscopy, such as gastroscopy or colonoscopy (for example, the diagnosis of esophageal cancer and gastric cancer through a gastroscope, and colorectal cancer through a colonoscope), or minimally invasive surgery, such as laparoscopic or robotic surgery (for example, the diagnosis of cancers with peritoneal and lymph node metastases during laparoscopic surgery), in a rapid and simple manner.

2. Description of the Related Art

Changes associated with neoplasia are used to determine the diagnosis, treatment, and recurrence of tumors. Biomarkers have been most extensively studied in the diagnosis of tumors using changes associated with neoplasia. Many biomarkers have been proposed, but only a few thereof are reproduced in actual clinical practice. This is believed to be because the number of methods for diagnosing biomarkers expressed in some living cells in a simple manner within a short time is not sufficient. Heterogeneity in cancer tissue is responsible for the limited use of biomarkers. Different types of biomarkers are expressed at different levels from person to person in the same type of tumor (intertumoral heterogeneity) and even in a single tumor (intratumoral heterogeneity). However, such heterogeneities of tumors are not reflected in current diagnostic methods using biomarkers in small tissue sections. Thus, there is a need for a new method for detecting changes occurring in tumors while reflecting the heterogeneities of tumors.

Many efforts have been made to develop optical imaging systems and tumor-specific fluorophores for clinical applications (Troyan, S. L. et al. The FLARE intraoperative near-infrared fluorescence imaging system: a first-in-human clinical trial in breast cancer sentinel lymph node mapping. *Ann. Surg. Oncol.* 16, 2943-2952 (2009); Luker, G. D. & Luker, K. E. Optical imaging: current applications and future directions. *J. Nucl. Med.* 49, 1-4 (2008); Tromberg, B. J. et al. Assessing the future of diffuse optical imaging technologies for breast cancer management. *Med. Phys.* 35, 2443-2451 (2008)), and their potential applicability to imaging-guided diagnostic and surgical methods has been proposed in several preclinical studies (Kirsch, D. G. et al. A spatially and temporally restricted mouse model of soft tissue sarcoma. *Nat. Med.* 13, 992-997 (2007); von Burstin, J. et al. Highly sensitive detection of early-stage pancreatic cancer by multimodal near-infrared molecular imaging in living mice. *Int. J. Cancer* 123, 2138-2147 (2008)), and clinical studies (Sevick-Muraca, E. M. et al. Imaging of lymph flow in breast cancer patients after microdose administration of a near-infrared fluorophore: feasibility study. *Radiology* 246, 734-741 (2008); Tagaya, N. et al. Intraoperative identification of sentinel lymph nodes by near-infrared fluorescence imaging in patients with breast cancer. *Am. J. Surg.* 195, 850-853 (2008); Stummer, W. et al. Fluorescence-guided surgery with 5-aminolevulinic acid for resection of malignant glioma: a randomised controlled multicentre phase III trial. *Lancet Oncol.* 7, 392-401 (2006)). Particularly, non-invasive methods based on optical imaging are advantageous in that in vivo changes can be observed in real time and continuously, and possess other advantages of high sensitivity, fast measurement, and rapid imaging processing.

However, the technologies reported to date are generally associated with targeting to receptors specifically expressed in tumor cells, detection of low pH around tumors, or production of contrast agents targeting particular enzymes over-distributed around tumors. To the best of our knowledge, no attempts have been reported to specifically image tumors by taking advantage of the ability of drugs to penetrate tumor cells and non-tumor cells at different rates or levels.

SUMMARY OF THE INVENTION

Therefore, the present invention has been made to fulfill the above needs recognized in the prior art, and it is an object of the present invention to provide a drug-fluorophore complex for specific detection of tumor cells, in which a tumor cell-targeting drug is conjugated to a fluorescent substance useful for use in in vivo imaging so that tumor cells only can be specifically imaged by a simple application technique, such as spraying, without causing cytotoxicity.

According to the present invention, there is provided a drug-fluorophore complex including a tumor cell-targeting drug penetrating tumor cells and non-tumor cells at different rates or levels, and a fluorescent substance chemically bonded to the tumor cell-targeting drug.

In one embodiment of the present invention, the drug-fluorophore complex may be any one of the compounds represented by Formulae 1 to 5:

(1)

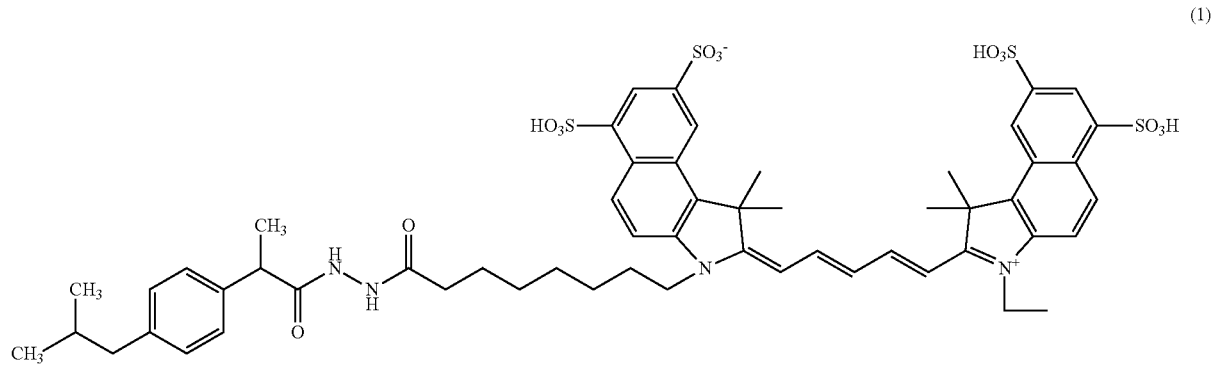

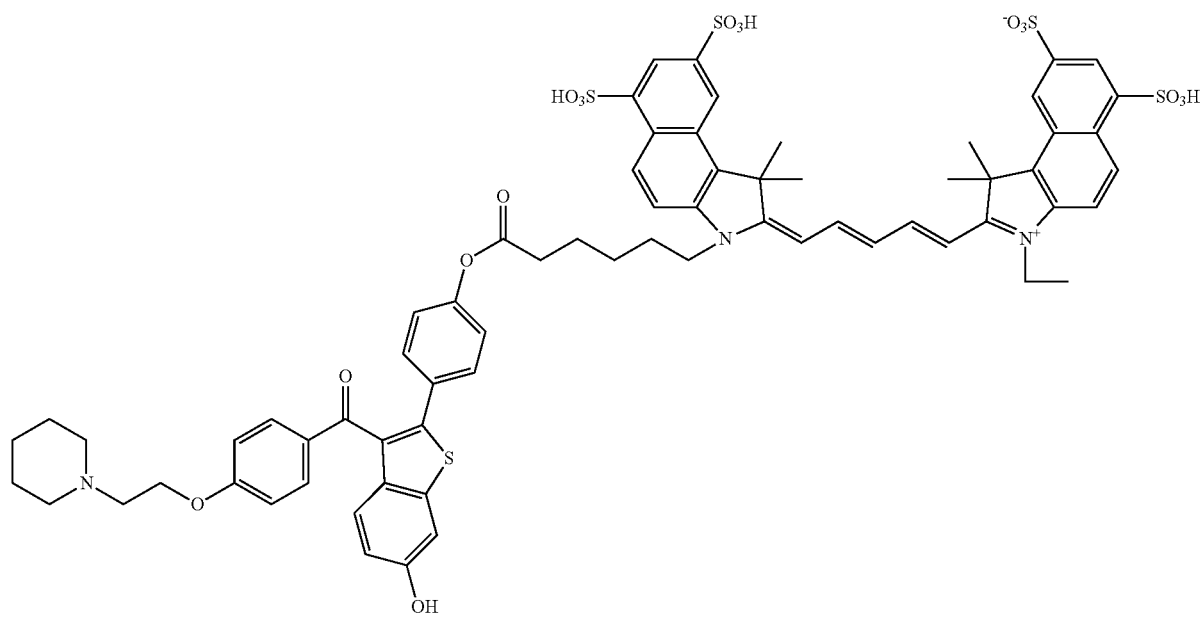
(2)
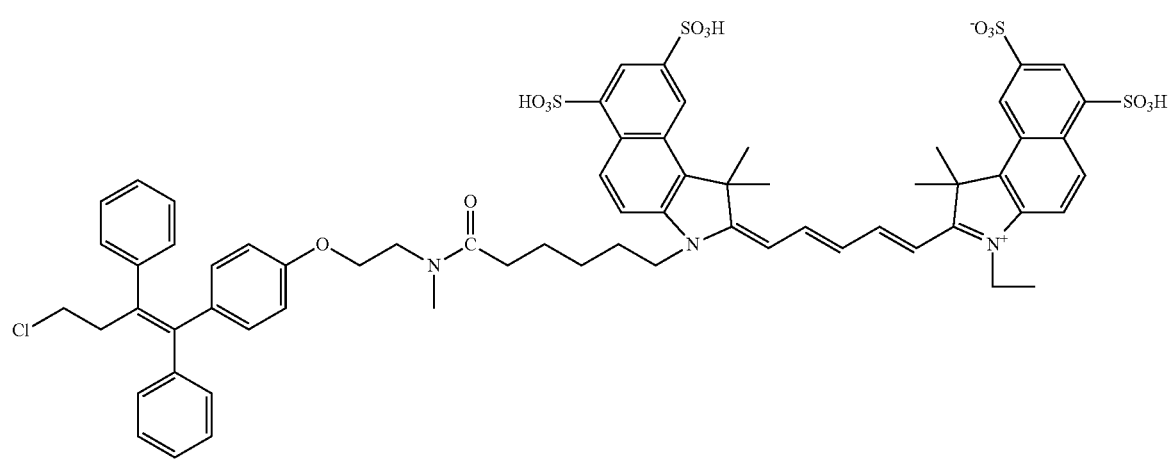
(3)
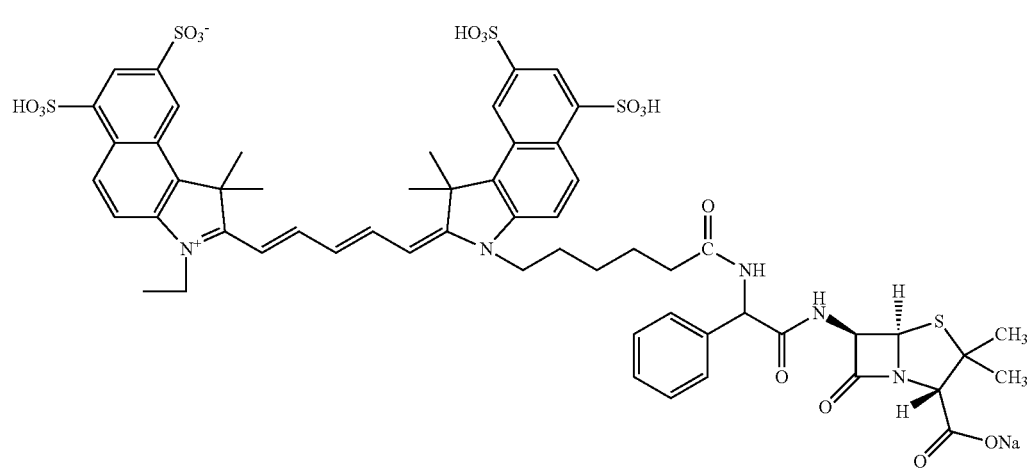
(4)

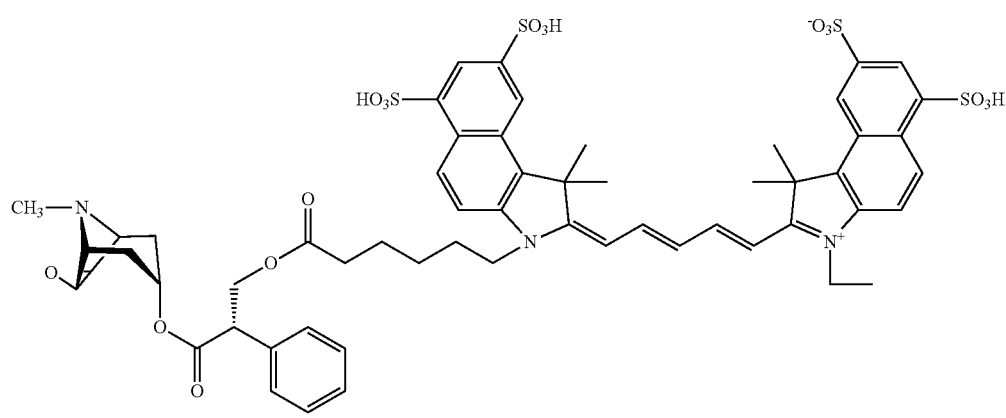

(5)

In a further embodiment of the present invention, the tumor cell-targeting drug may be ibuprofen, ampicillin, scopolamine, N-desmethyltoremifene, or raloxifene.

In another embodiment of the present invention, the fluorescent substance may be fluorescein, BODIPY, tetramethylrhodamine, Alexa, cyanine, allophycocyanin, or a derivative thereof.

In another embodiment of the present invention, the fluorescent substance may be a fluorophore emitting fluorescence in the visible or near-infrared region.

In another embodiment of the present invention, the drug-fluorophore complex may take the form of a spraying dye that is sprayable onto tumor cell sites during surgery.

In another embodiment of the present invention, the tumor cells may be cells of at least one cancer selected from the group consisting of gastric cancer, esophageal cancer, colorectal cancer, and liver cancer.

The drug-fluorophore complex of the present invention enables specific imaging of tumor cells only with high accuracy in a very simple manner without causing cytotoxicity during surgery.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE INVENTION

Figure 1A:
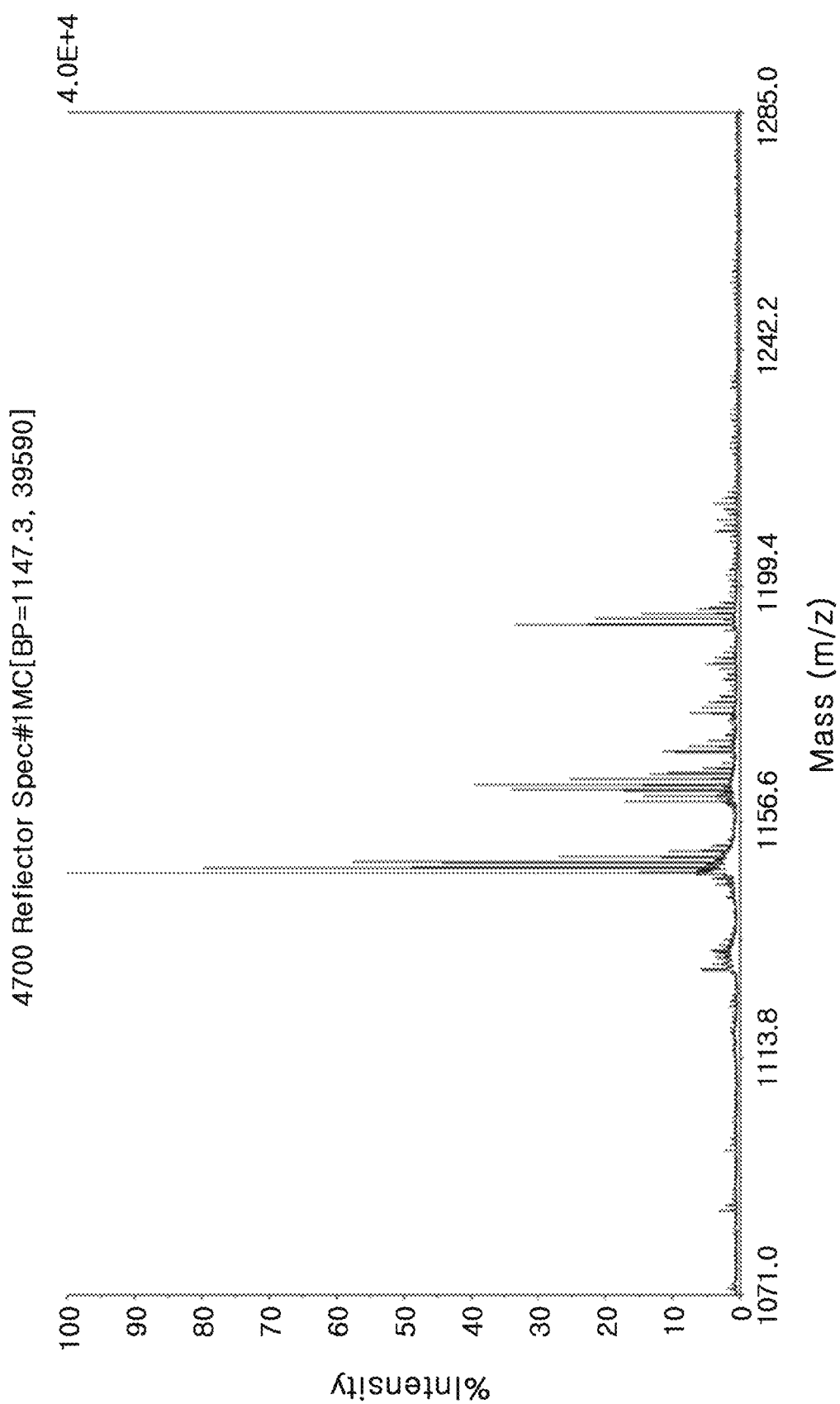
FIGS. 1a to 1e are graphs showing the results of MALDI-TOF mass analysis for drug-fluorophore complexes according to the present invention.

The present invention will now be described in more detail.

The present invention provides a drug-fluorophore complex in which a fluorescent marker advantageous for in vivo imaging is bonded to a general therapeutic drug for tumor.

The drug-fluorophore complex of the present invention enables specific imaging of tumor cells only without causing cytotoxicity, unlike conventional methods for the detection of tumor cells by targeting receptors, detecting pH around tumor cells, or targeting particular tumor-specific enzymes.

Specifically, the complex of the present invention includes a tumor cell-targeting drug penetrating tumor cells and non-tumor cells at different rates or levels, and a fluorescent substance chemically bonded to the tumor cell-targeting drug.

The tumor cell-targeting drug of the complex according to the present invention may be any of those that are commonly used to treat tumor cells in the art. Drugs have different penetration kinetics or penetration depths due to structural features of tumors, tumor satellites, and non-tumors. A drug having high degree of tissue penetration is preferably used in the present invention. Specific examples of such drugs include, but are not limited to, ibuprofen, ampicillin, scopolamine, N-desmethyltoremifene, and raloxifene.

Table 1 shows the molecular weights and volumes of distribution of exemplary tumor cell-targeting drugs suitable for use in the present invention.

TABLE 1

| Targeting drug | Ibuprofen | Ampicillin | Scopolamine | N-desmethyltoremifene | Raloxifene |
| --- | --- | --- | --- | --- | --- |
| Molecular weight | 206.29 | 349.41 | 303.35 | 391.93 | 473.58 |
| Volume of distribution (L/kg) | 0.1 | 0.38 | 1.4 | 8.3 | 2348 |

The fluorescent substance as another component of the complex according to the present invention emits fluorescence in the visible or near-infrared region. A near-infrared fluorescent substance is particularly advantageous for in vivo imaging because near-infrared light is less absorbed by hemoglobin or oxygen, which contributes to a reduction in fluorescence background.

Specific examples of fluorescent substances suitable for use in the present invention include fluorescein, BODIPY, tetramethylrhodamine, Alexa, cyanine, allophycocyanin, other fluorescence-emitting fluorophores, and derivatives thereof. The use of fluorophores with high quantum yield is also preferred. Cyanine- and Alexa-based fluorescent substances are particularly preferred due to their ability to emit and absorb near-infrared light (650-900 nm), which contributes to the minimization of interference with and absorption by cells, blood, living tissues, etc.

In the drug-fluorophore complex of the present invention, the tumor cell-targeting drug is chemically bonded to the fluorescent substance such as ibuprofen, ampicillin, scopolamine, N-desmethyltoremifene or raloxifene, as described above. Specifically, the drug-fluorophore complex of the present invention may be any one of the compounds represented by the following formulae 1 to 5:

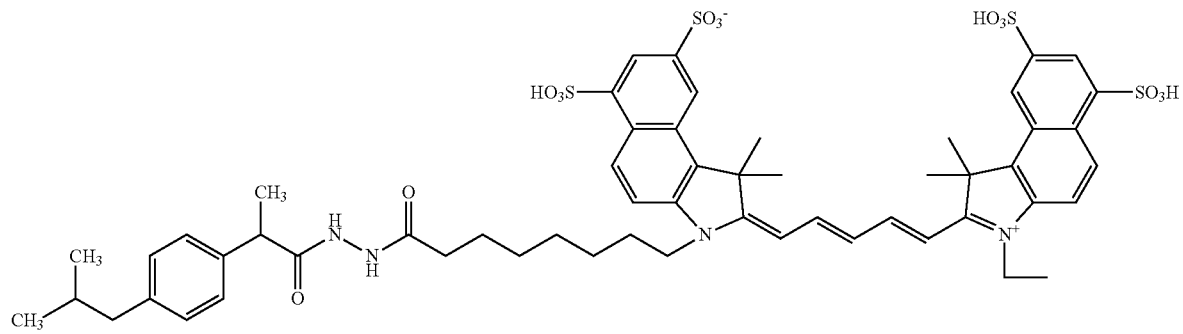

(1)

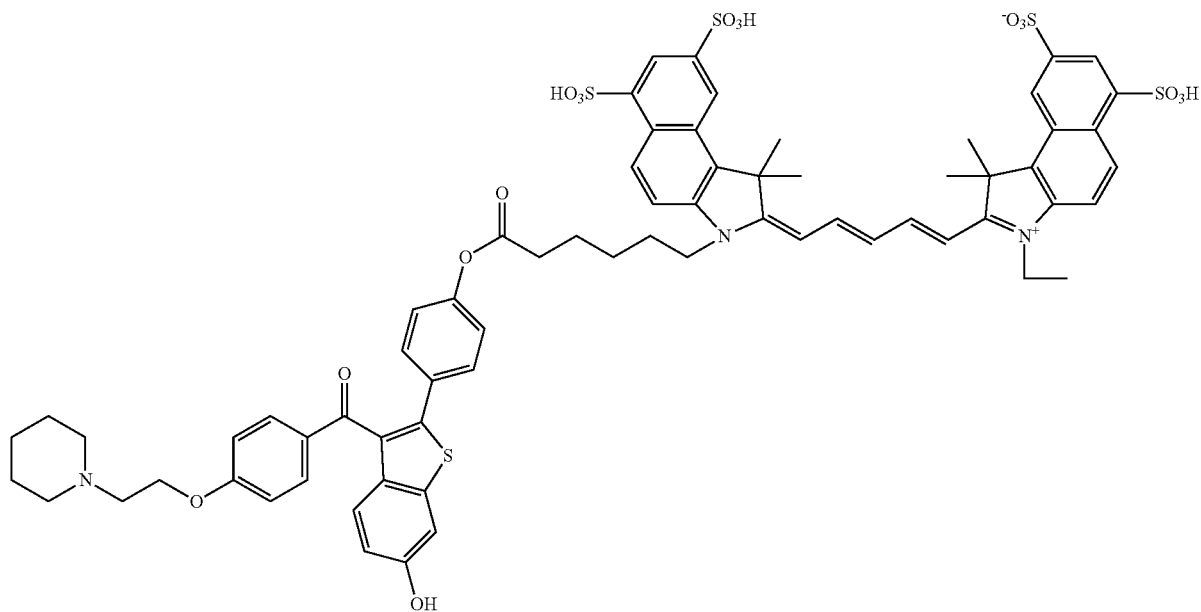

(2)

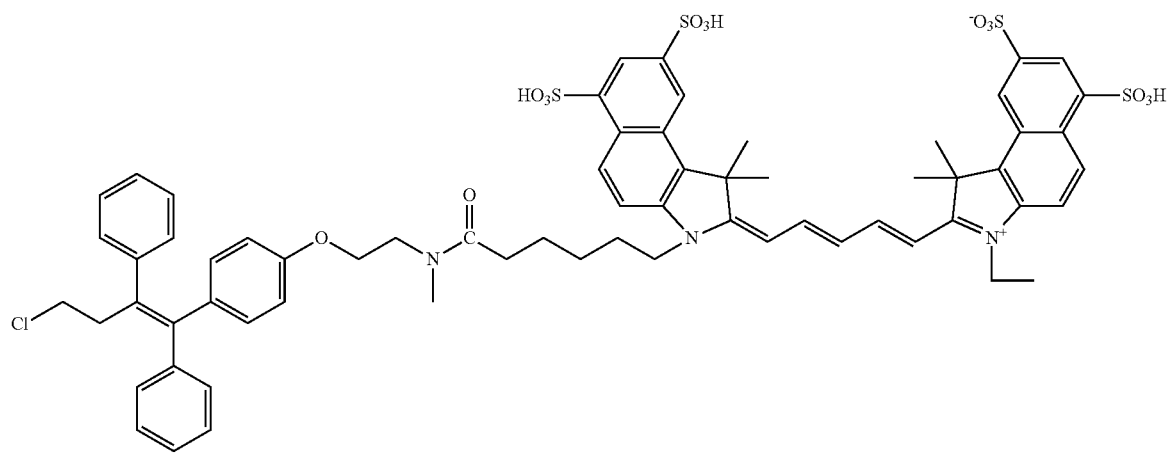

(3)

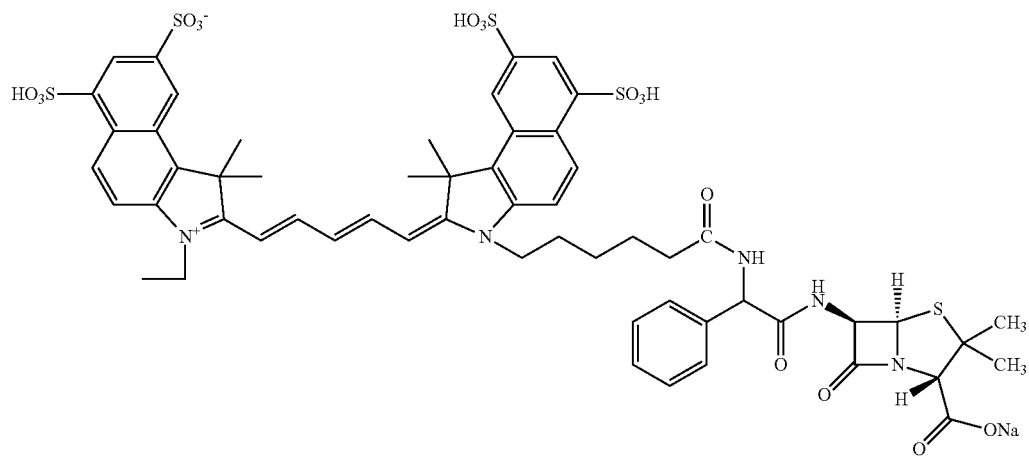

(4)

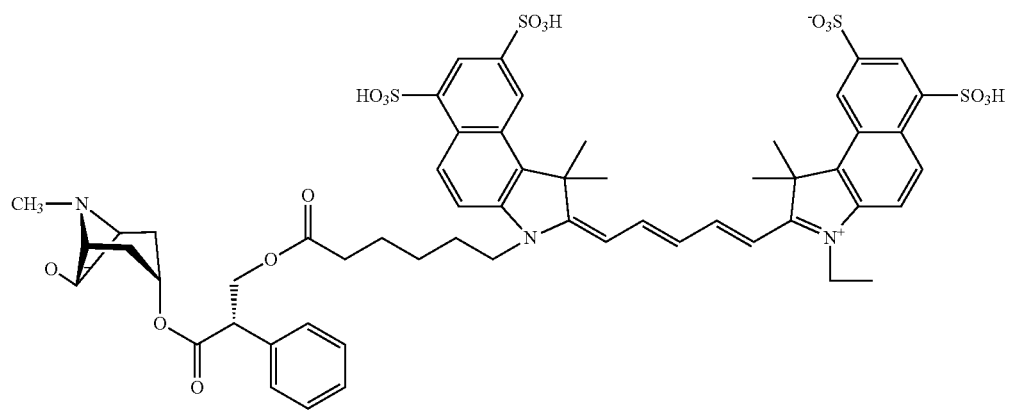

(5)

The drug-fluorophore complex of the present invention can be prepared into various shapes that are applicable to tumor cell sites. For example, the drug-fluorophore complex of the present invention may also take the form of a spraying dye that is sprayable onto tumor cell sites during surgery, but is not limited to this form.

The tumor cells, to which the drug-fluorophore complex of the present invention is applicable, may be cells of at least one cancer selected from the group consisting of, but not limited to, gastric cancer, esophageal cancer, colorectal cancer, and liver cancer.

The present invention will be explained in more detail with reference to the following examples. However, these examples are provided to assist in a further understanding of the invention and are not intended to limit the scope of the invention.

Synthesis of Drug-Fluorophore Complexes
Reagents and Suppliers
Raloxifene: Sigma-Aldrich
N-desmethyltoremifene: Toronto Research Chemicals Inc.
Scopolamine: Sigma-Aldrich
Ampicillin sodium salt: Sigma-Aldrich
Ibuprofen: Sigma-Aldrich
N,N'-Diisopropylcarbodiimide (DIC): Sigma-Aldrich
4-Dimethylaminopyridine (DMAP): Sigma-Aldrich
N,N-Diisopropylethylamine (DIPEA): Sigma-Aldrich
O-(7-azabenzotriazol-1-yl)-N,N,N',N'-tetramethyluroniumhexafluorophosphate (HATU): Sigma-Aldrich
DMF: Sigma-Aldrich
FCR675 Carboxylic acid: BioActs
FCR675 Amine: BioActs
FNR675 NHS-ester: BioActs

SYNTHESIS EXAMPLE 1

Synthesis of the Complex of Formula 1

Ibuprofen-FCR675 Amine Complex

Ibuprofen (1 equiv.) was dissolved in DMF, and then DIPEA (2 equiv.) was added thereto. To the ibuprofen solution was added a solution of HATU (1.2 equiv.) in DMF. The mixture was activated for 10 min, followed by the addition of a solution of FCR675 amine (1.2 equiv.) in DMF. The resulting mixture was allowed to react at room temperature overnight. The compound of Formula 1 was isolated from the reaction mixture by HPLC.

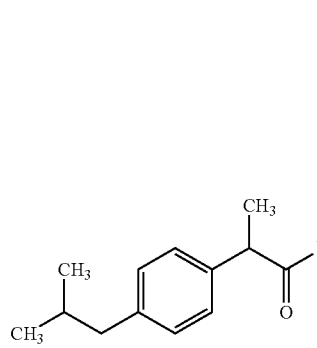
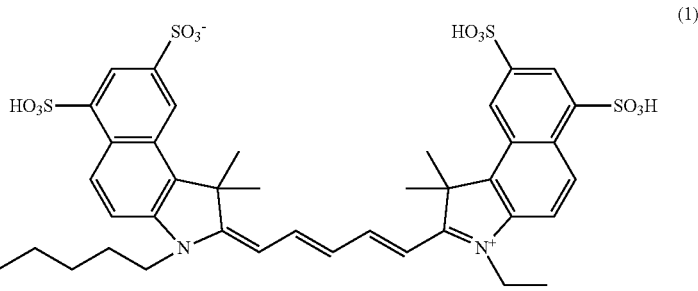

(1)

SYNTHESIS EXAMPLE 2

Synthesis of the Complex of Formula 2

Raloxifene-FCR675 Carboxylic Acid Complex

Raloxifene (1 equiv.) was dissolved in DMF and desalted for 10 min by the addition of TEA (6 equiv.). FCR675 carboxylic acid (2 equiv.) was dissolved in DMF and activated for 10 min by the addition of DIC (2 equiv.). DMAP (0.2 equiv.) was added to the FCR675 carboxylic acid solution and immediately added to the raloxifene solution. The resulting mixture was allowed to react at room temperature overnight. The compound of Formula 2 was isolated from the reaction mixture by HPLC.

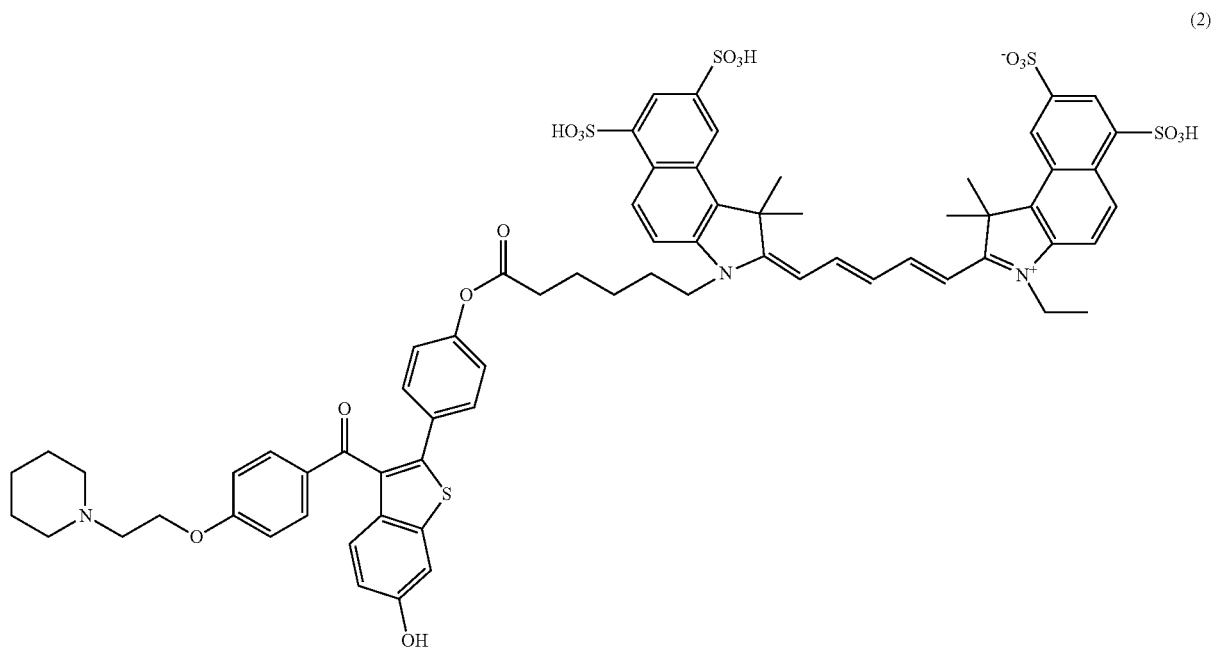

(2)

SYNTHESIS EXAMPLE 3

Synthesis of the Complex of Formula 3

N-desmethyl toremifene-FCR675 Carboxylic Acid Complex

FCR675 carboxylic acid (1 equiv.) was dissolved in DMF, and then DIPEA (2 equiv.) was added thereto. To the FCR675 carboxylic acid solution was added a solution of HATU (1.2 equiv.) in a minimum amount of DMF, followed by activation for 10 min. The FCR675 carboxylic acid solution was added to a solution of N-desmethyltoremifene (1.2 equiv.) in DMF. The resulting mixture was allowed to react at room temperature overnight. The compound of Formula 3 was isolated from the reaction mixture by HPLC.

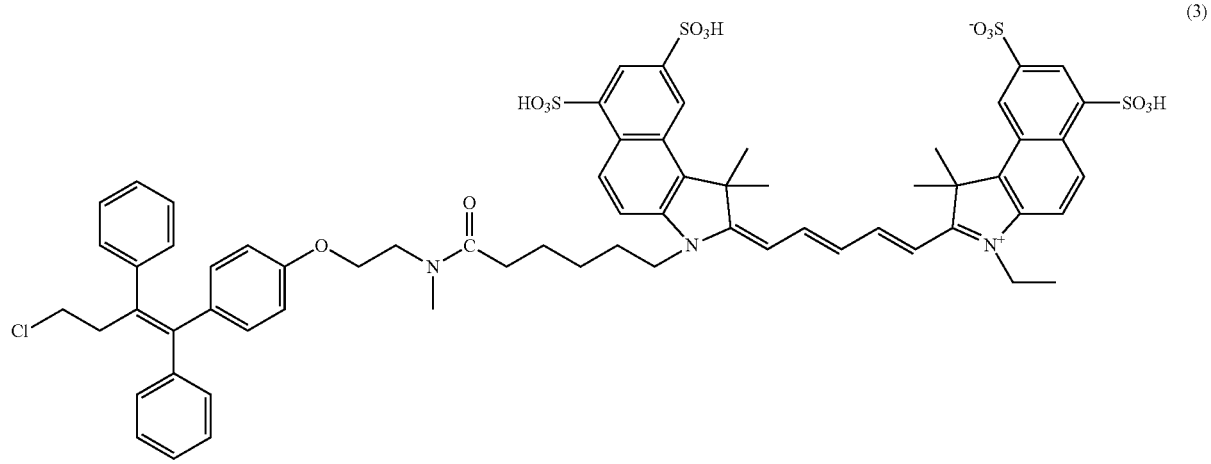

(3)

SYNTHESIS EXAMPLE 4

Synthesis of the Complex of Formula 4

Ampicillin Sodium-FCR675 NHS Ester Complex

Ampicillin sodium (1.2 equiv.) was dissolved in DMF. FCR675 NHS ester (1 equiv.) was dissolved in DMF. The FCR675 NHS ester solution was added to the ampicillin sodium solution. The mixture was allowed to react at room temperature for 3 h. The compound of Formula 4 was isolated from the reaction mixture by HPLC.

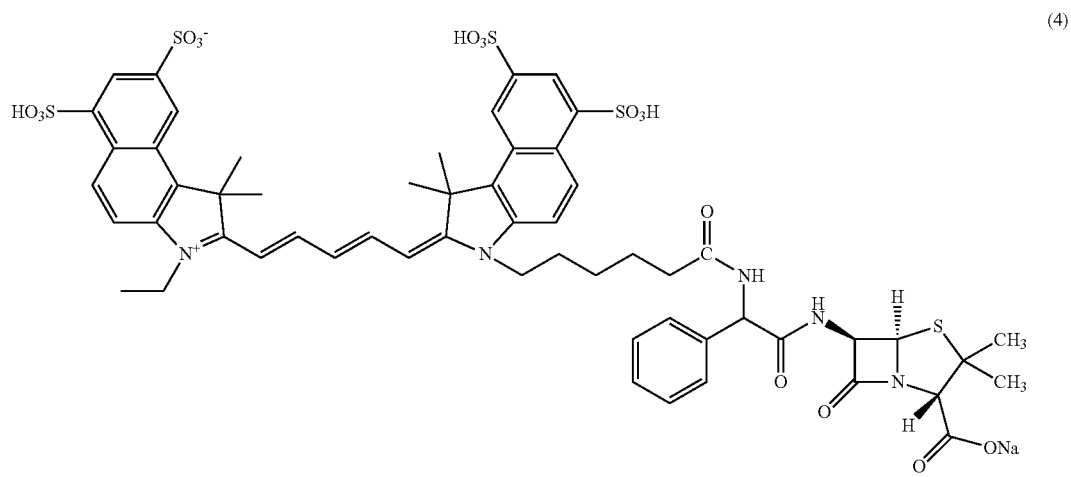

(4)

SYNTHESIS EXAMPLE 5

Synthesis of the Complex of Formula 5

Scopolamine-FCR675 Carboxylic Acid Complex

Scopolamine (1 equiv.) was dissolved in DMF and desalted for 10 min by the addition of TEA (6 equiv.). FCR675 carboxylic acid (2 equiv.) was dissolved in DMF and activated for 10 min by the addition of DIC (2 equiv.). DMAP (0.2 equiv.) was added to the FCR675 carboxylic acid solution and immediately added to the scopolamine solution. The resulting mixture was allowed to react at room temperature overnight. The compound of Formula 5 was isolated from the reaction mixture by HPLC.

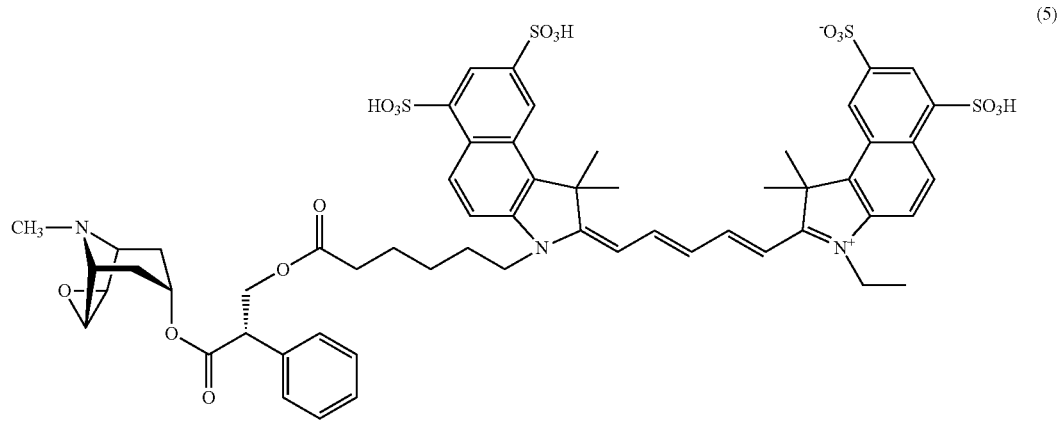

(5)

Figure 1B:
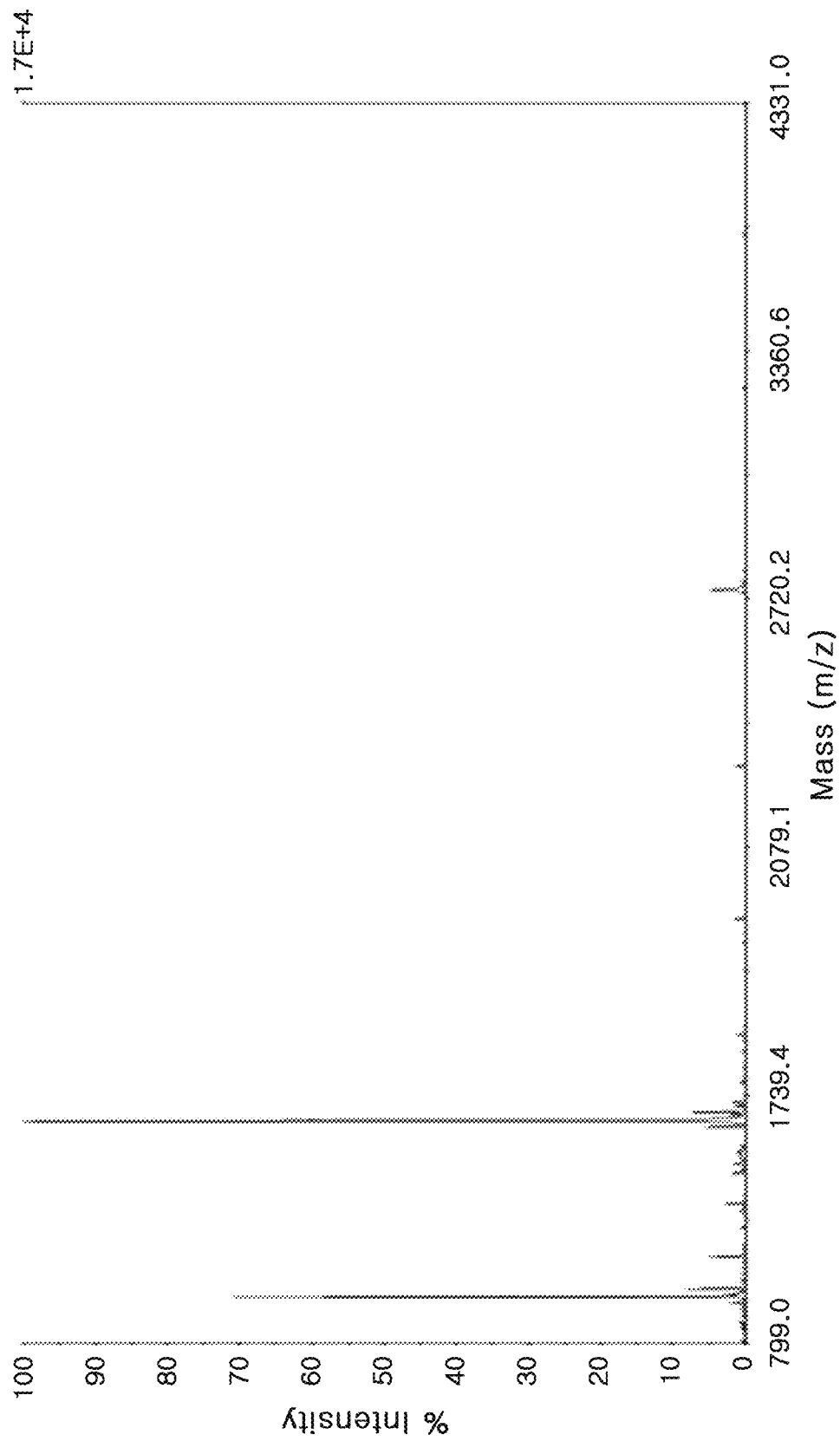
Figure 1C:
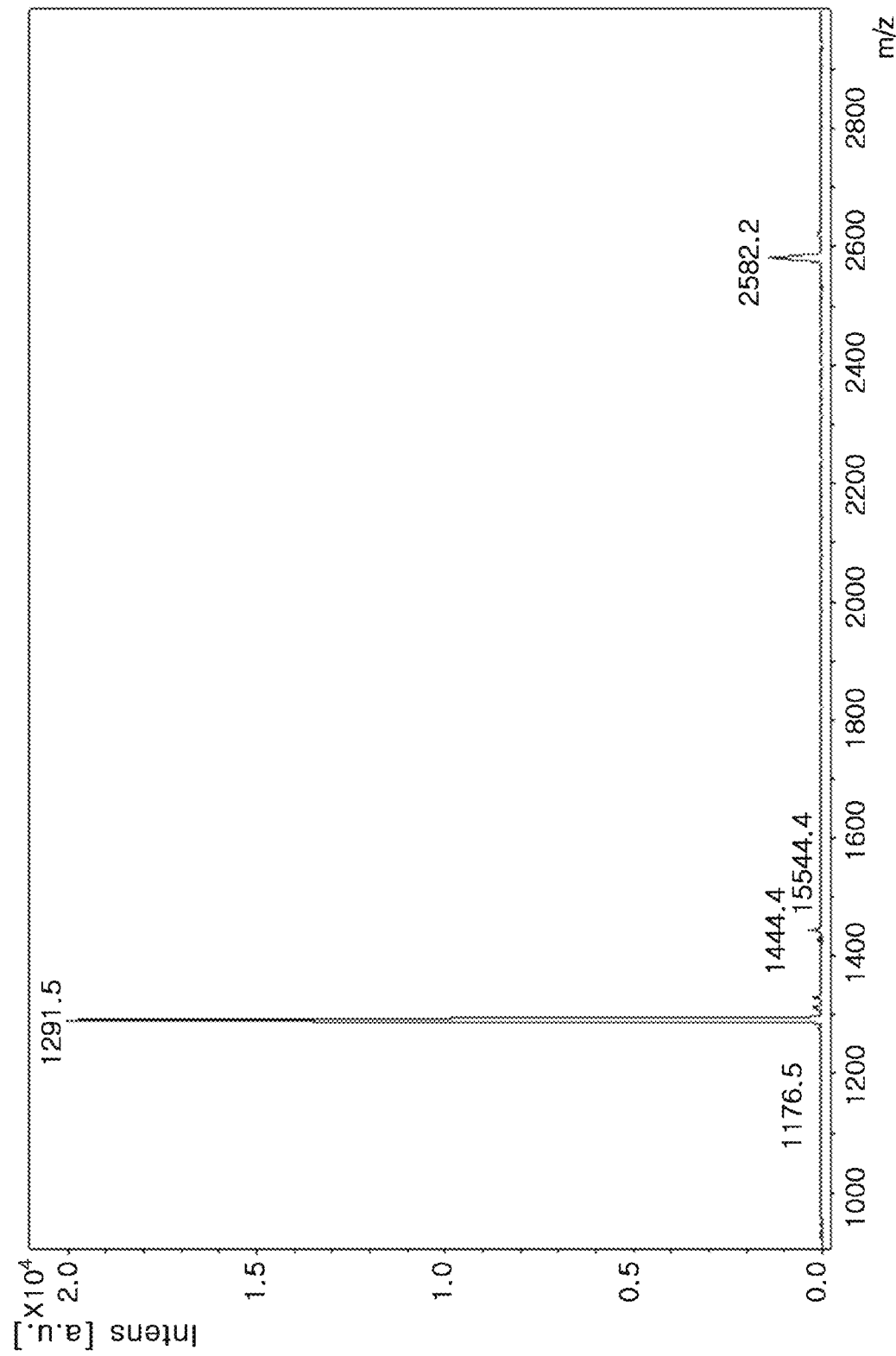
Figure 1D:
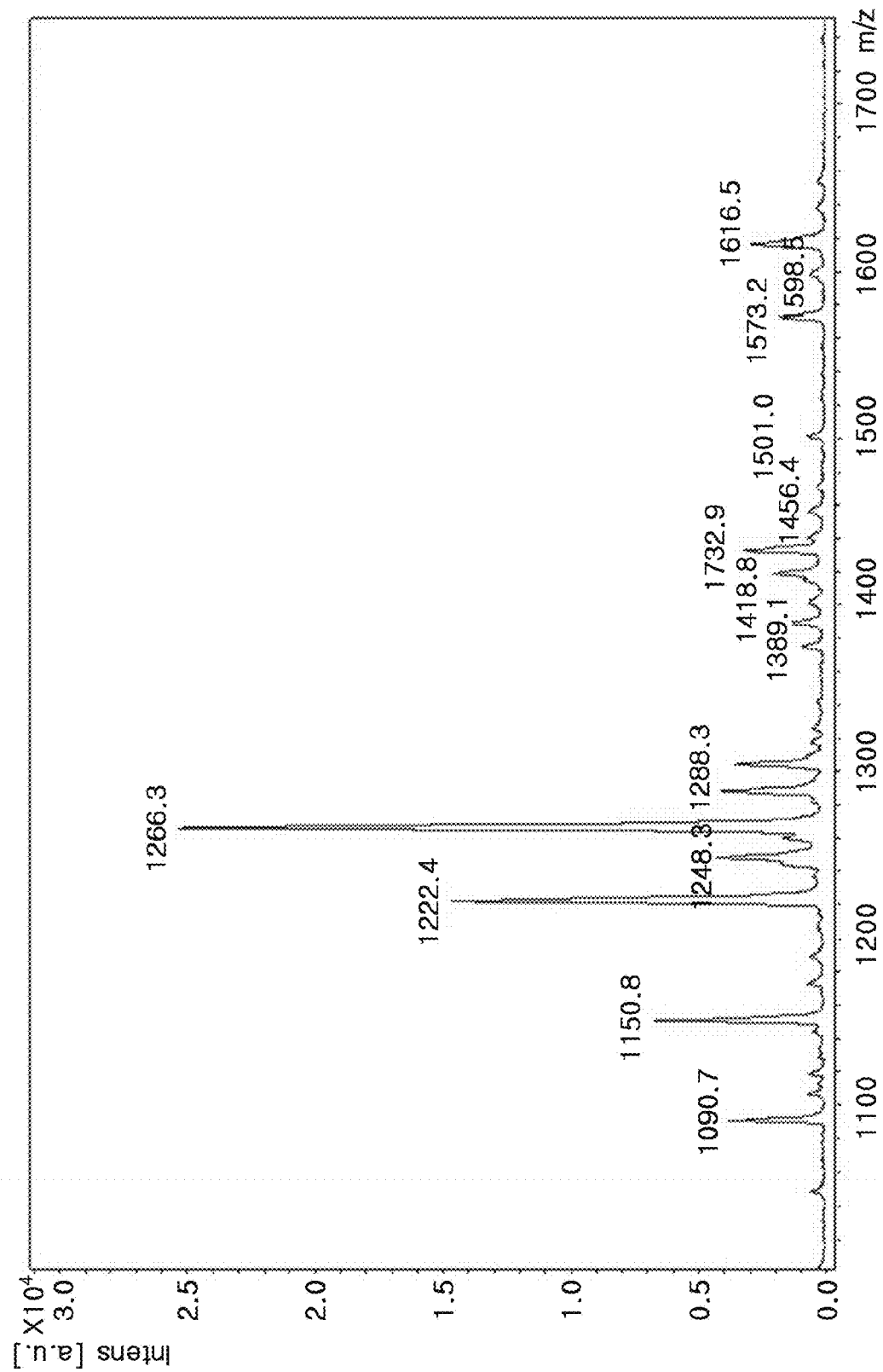
Figure 1E:
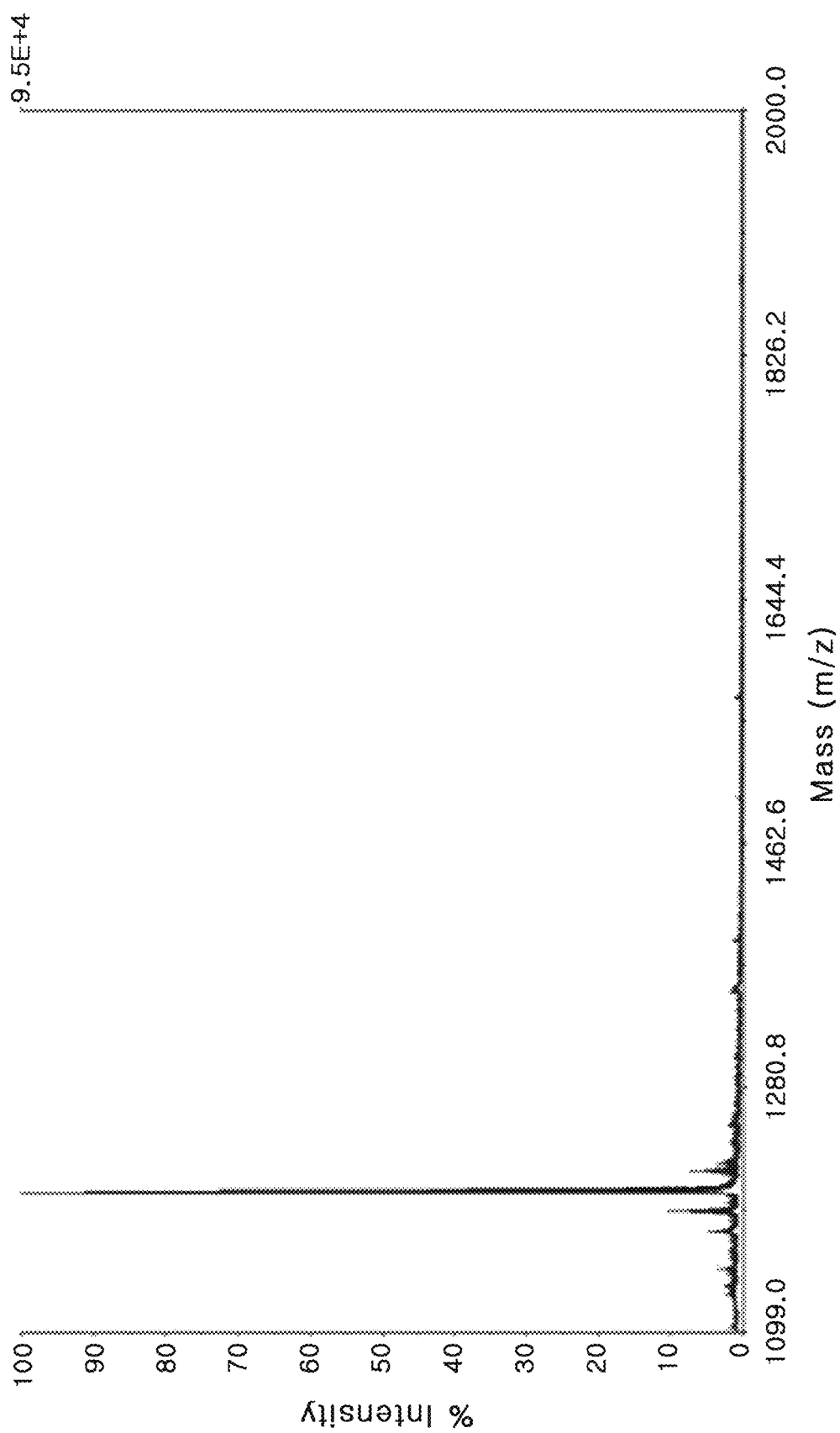

The compounds thus synthesized were subjected to MALDI-TOF mass analysis. The results of analysis are shown in FIGS. 1a to 1e. Comparison of the structures of Formulae 1-5 and the obtained mass analysis data reveals that the compounds of Formulae 1-5 were successfully synthesized.

Cytotoxicity of Complexes

MTT assay was conducted to test the cytotoxicity of the complexes.

First, 200 µl of HT-29 cells at a concentration of $2.5 \times 10^4$/ml were plated in each well of a 96-well plate. Each of the five compounds prepared in Synthesis Examples 1-5 was dissolved in PBS to prepare solutions having concentrations of 2.5 µM, 5 µM, 10 µM, 25 µM, 50 µM, and 100 µM. The solutions (each 20 µl) were added to the wells (blank: medium 200 µl+PBS 20 µl; control: cell suspension 200 µl+PBS 20 µl). After 24-h culture, the samples were removed and an MTT solution was added to the wells (100 µl each well). Subsequently, after 4-h culture, the MTT solution was removed. 100 µl of DMSO was added to each well and mixed using a plate shaker for 15-20 min. The absorbance values of the mixtures at 540 nm were measured using an ELISA reader to evaluate the cytotoxicity of the compounds. As a result, the compounds of Synthesis Examples 1-5 showed no cytotoxicity at all concentrations.

Specific Imaging of Tumor Cells

Mice were anesthetized with intraperitoneal injection of ketamine and xylazine, and their abdomens were cut open. HCT-116 cells (colorectal cancer cells) including luciferase were added at a concentration of $1 \times 10^6$ cells to 20 µl saline solution and injected into the left lobe of the liver to induce tumors in the mice. Four weeks after cell injection, the tumors were imaged as follows:

The compounds of Synthesis Examples 1-5 were dissolved in PBS (pH 7.4) to prepare 25 µM solutions. Mice were anesthetized intraperitoneally and their abdomens were open. 50 µl of each of the compounds was dropped using a 100 µl pipette. After 3 min, fluorescence and luminescence were observed using an imaging system (IVIS®).

Figure 2A:
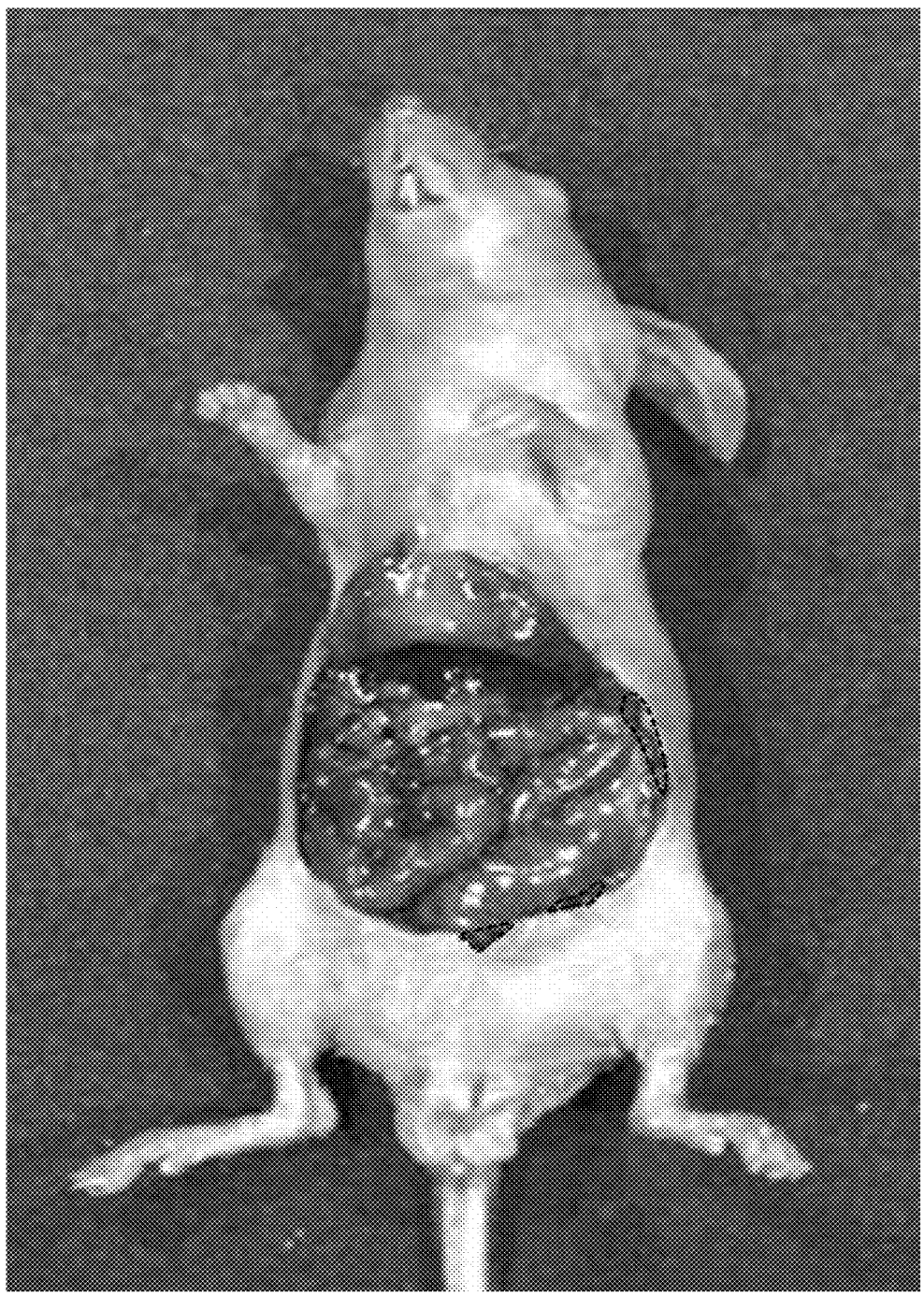
FIGS. 2a to 2d are images showing fluorescence (2a) and luminescence (2b) from a fluorophore to which toremifene was not bonded, and images showing fluorescence (2c) and luminescence (2d) from a complex of the present invention in which a fluorophore was bonded to toremifene.
Figure 2B:
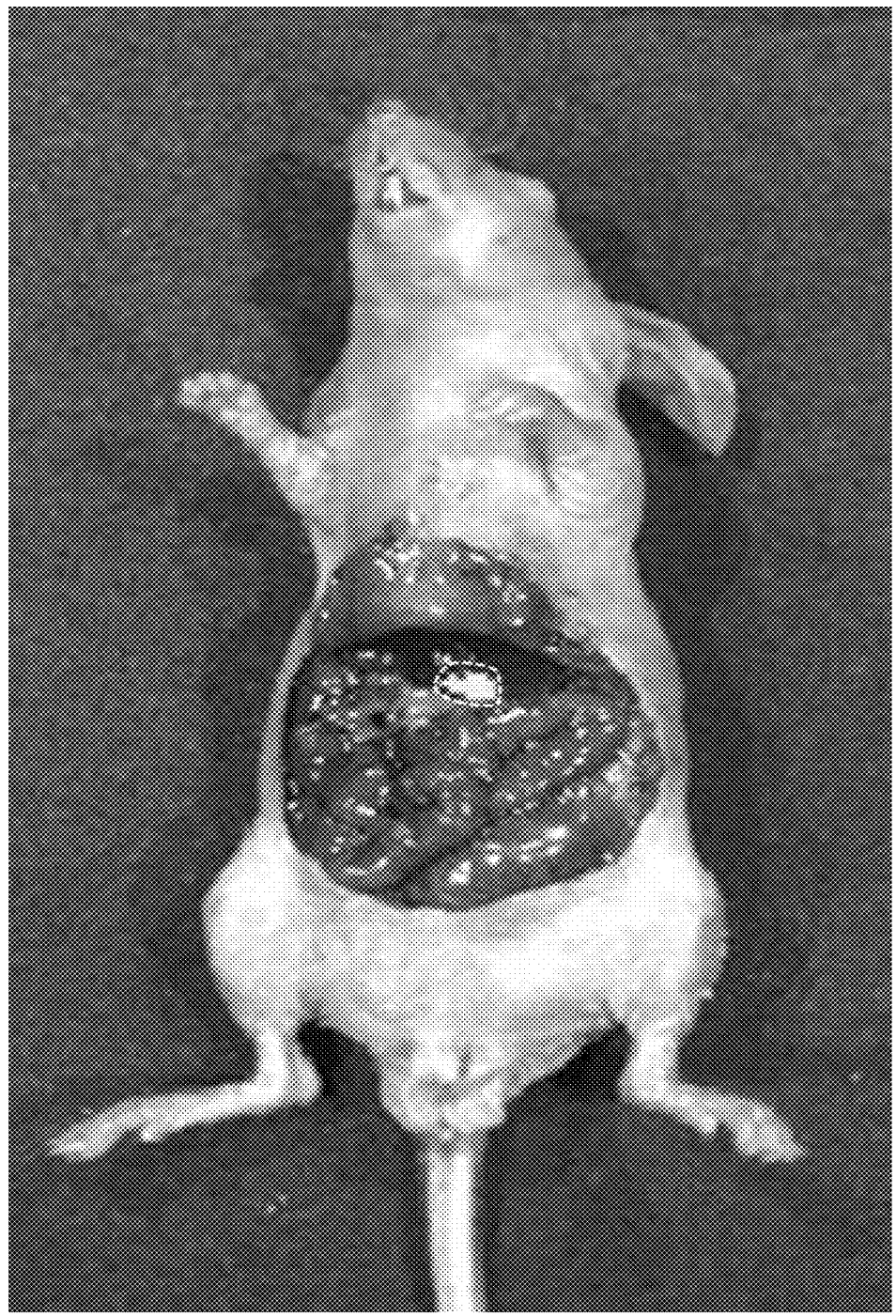
Figure 2C:
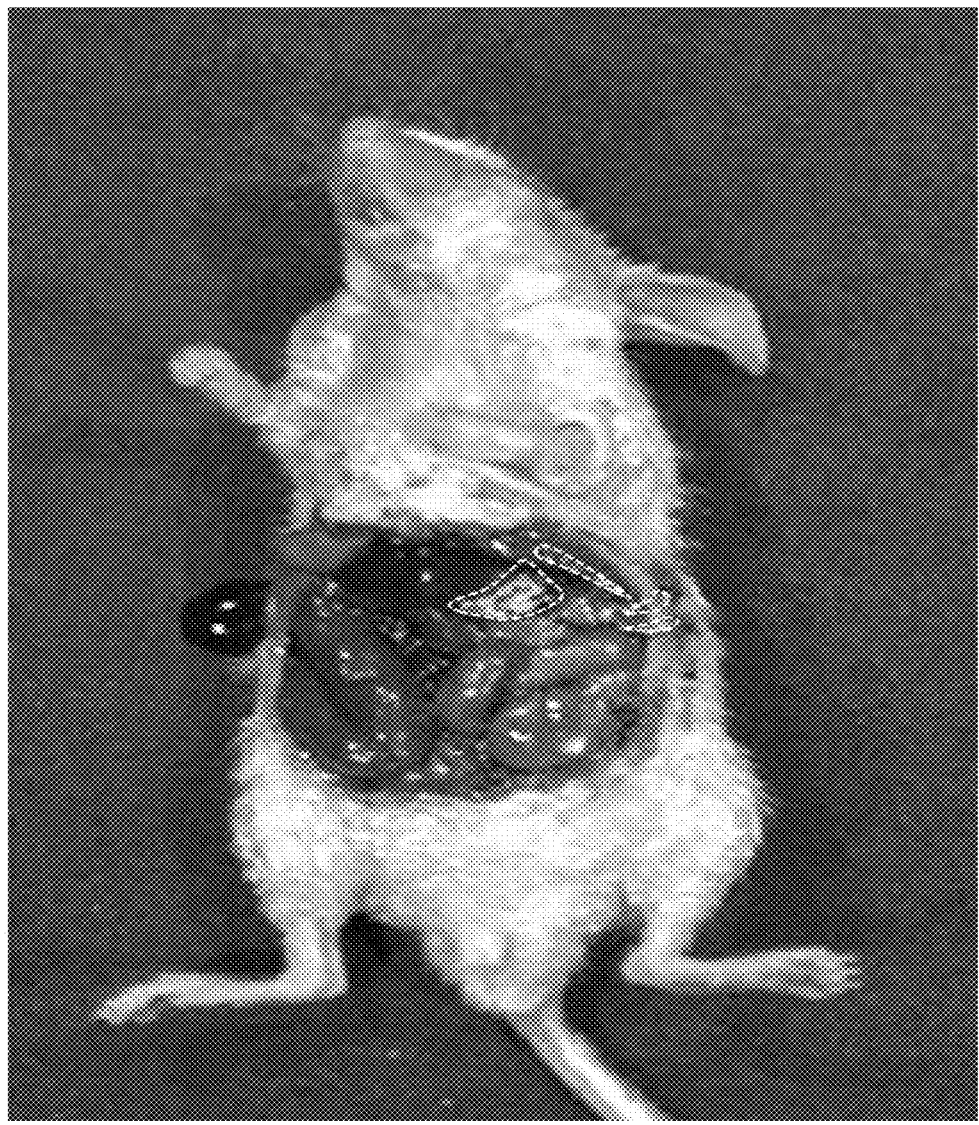
Figure 2D:
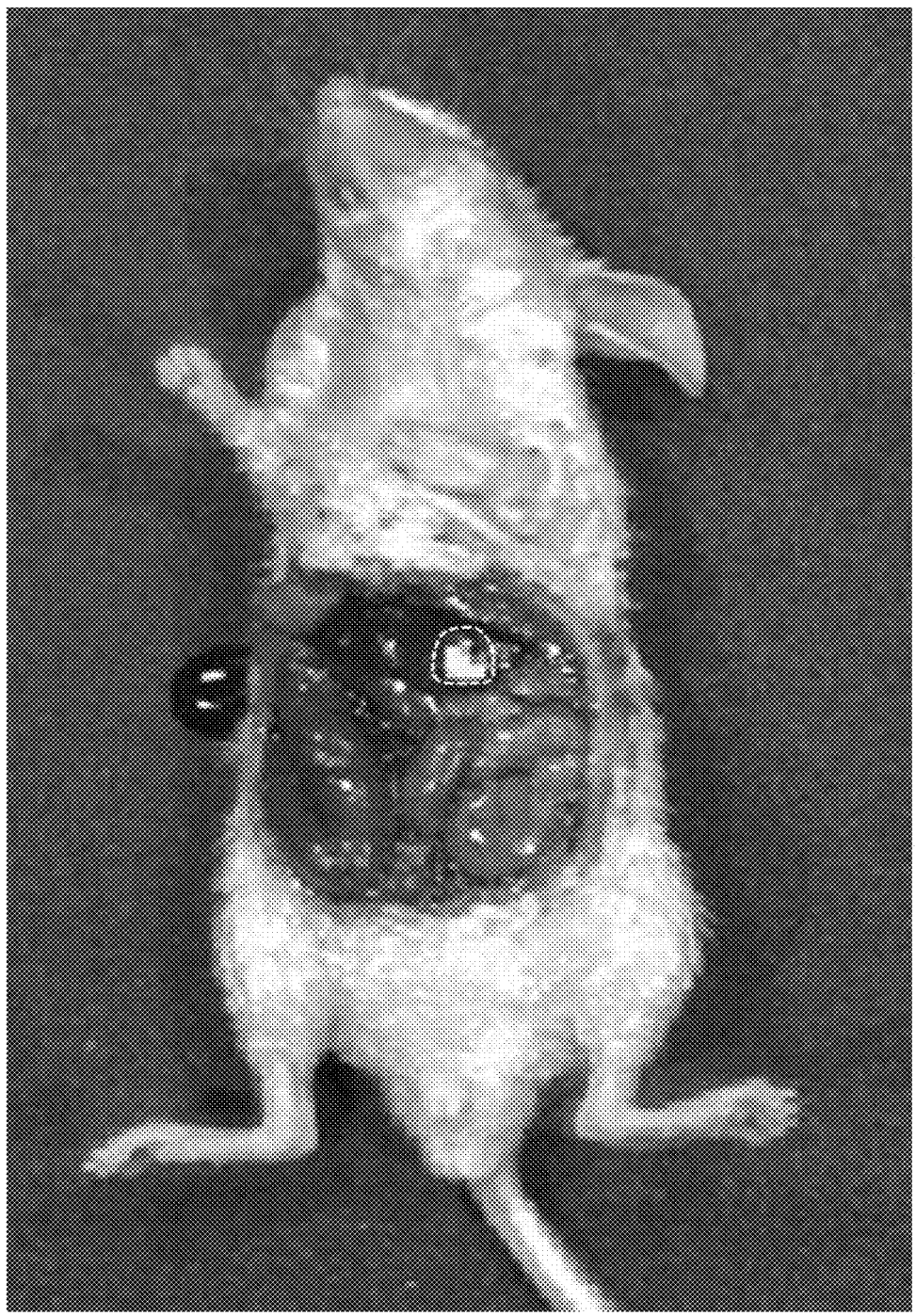

FIGS. 2a to 2d are images showing fluorescence (2a) and luminescence (2b) from the fluorophore to which toremifene was not bonded, and images showing fluorescence (2c) and luminescence (2d) from the complex of the present invention in which the fluorophore was bonded to toremifene. Referring to these figures, fluorescence did not substantially remain in the liver stained with the fluorophore to which the drug was not bonded. In contrast, when the drug-fluorophore complex of the present invention, in which the fluorophore was bonded to the drug, was used, fluorescence was observed in the section of the liver, which was the same as the position confirmed by luminescence.

Figure 3A:
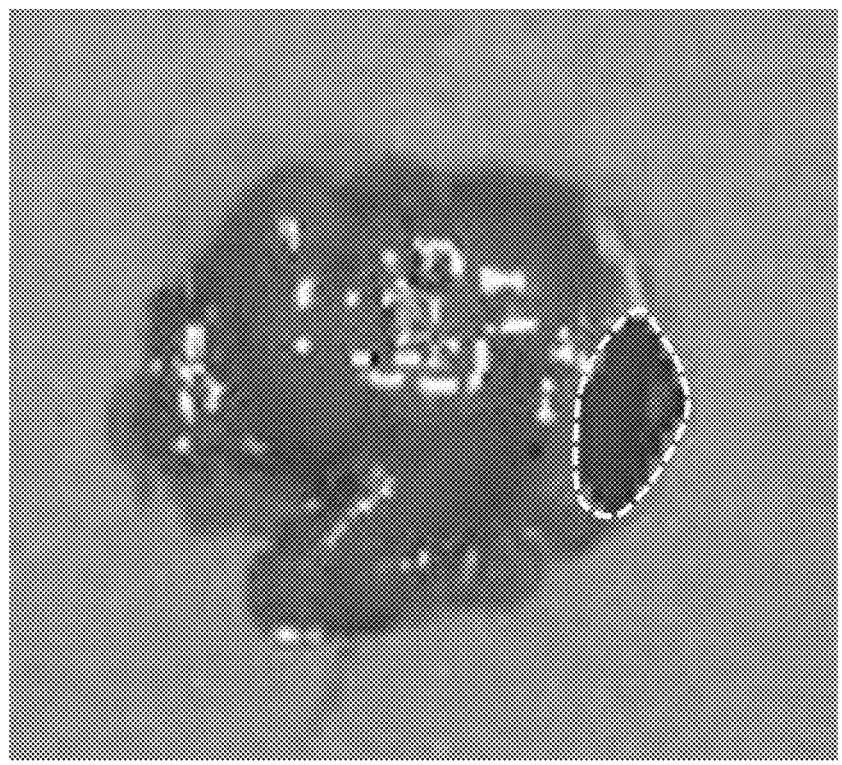
FIGS. 3a to 3d are ex vivo images of liver sections excised from mice; fluorescence (3a) and luminescence images (3b) of a fluorophore; and fluorescence (3c) and luminescence images (3d) of a drug-fluorophore complex.
Figure 3B:
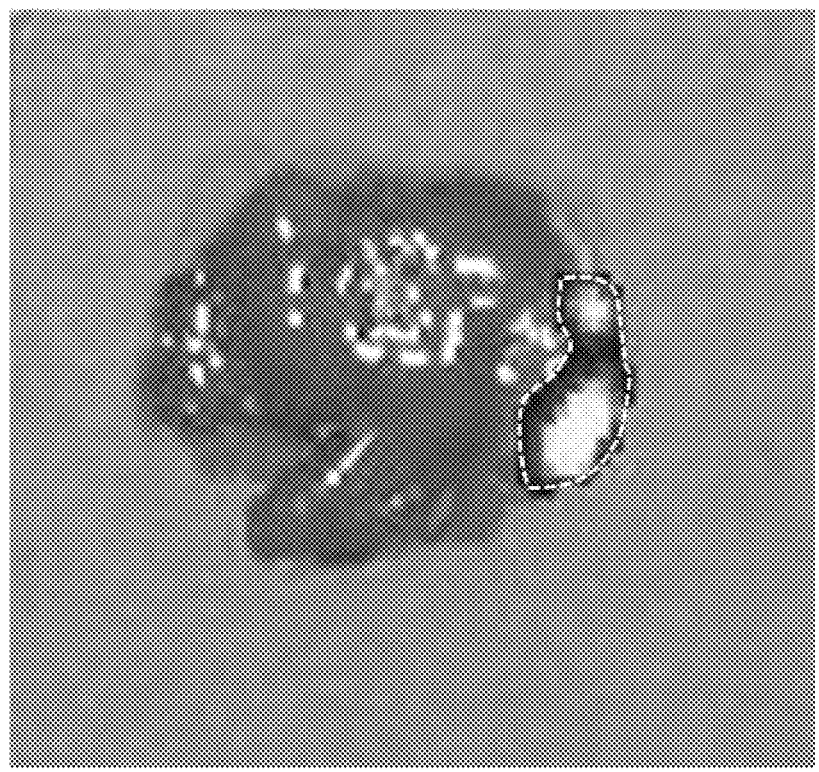
Figure 3C:
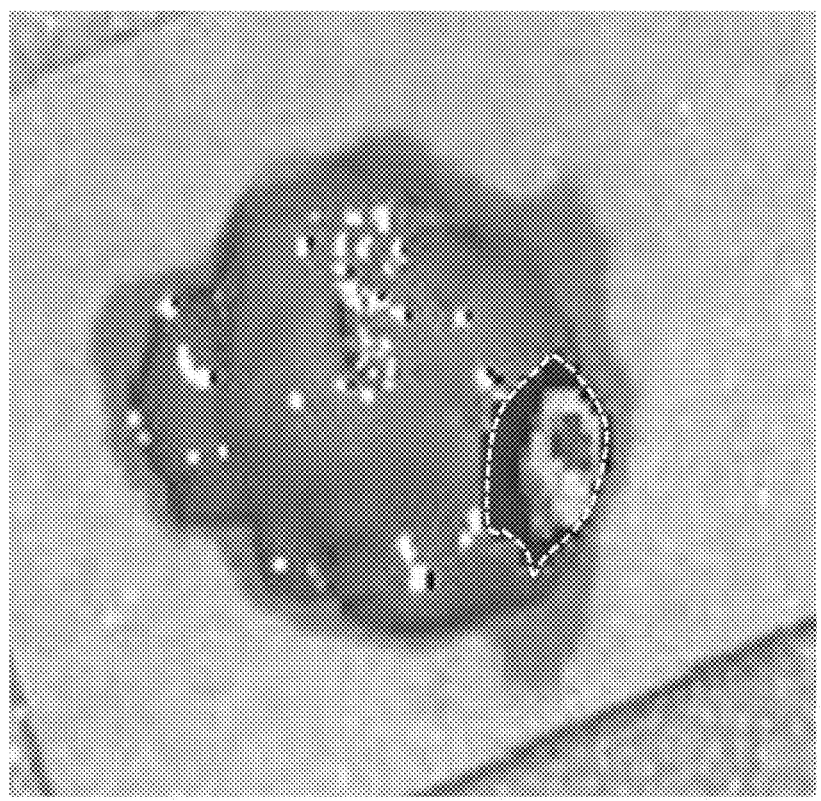
Figure 3D:
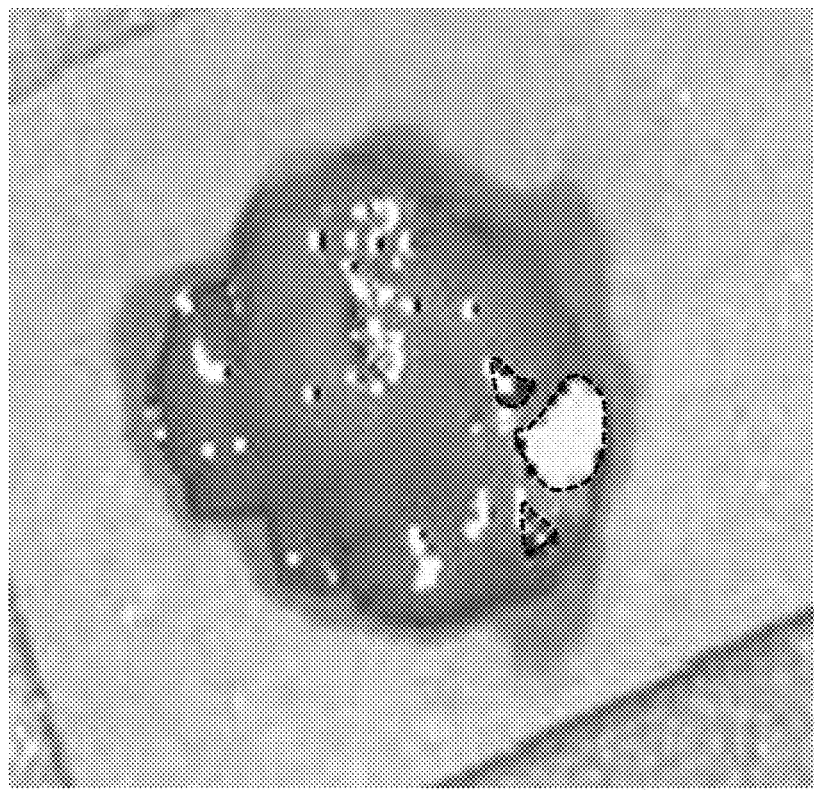

Similarly to the procedure described above, ex vivo imaging was performed on liver sections excised from mice. The results are shown in FIGS. 3a to 3d (3a and 3b: fluorescence and luminescence images of the fluorophore, respectively; 3c and 3d: fluorescence and luminescence images of the drug-fluorophore complex, respectively). As can be seen from FIGS. 3a to 3d, the same results of the in vivo imaging were observed in the ex vivo imaging.

What is claimed is:

1. A drug-fluorophore complex for specific detection, via in vivo imaging, of tumor cells at a tumor cell site during surgery, the drug-fluorophore complex comprising:
   a tumor cell-targeting drug penetrating tumor cells and non-tumor cells at different rates or levels; and
   a fluorescent substance chemically bonded to the tumor cell-targeting drug, wherein the drug-fluorophore complex is applied to the tumor cell site during surgery whereby tumor cells are detected via in vivo imaging in an efficient manner without causing cytotoxicity during surgery,
   wherein the drug-fluorophore complex is any one of the compounds represented by Formulae 1 to 5:

(1)

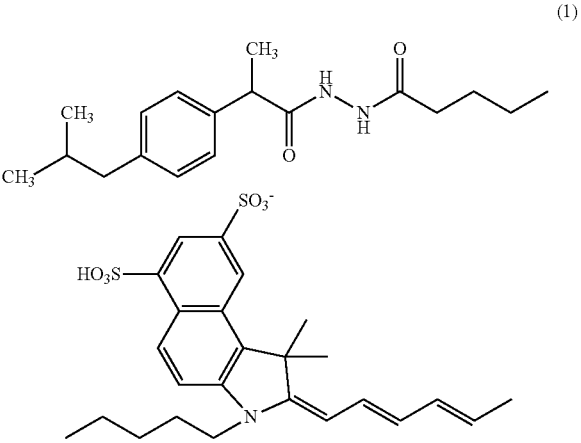

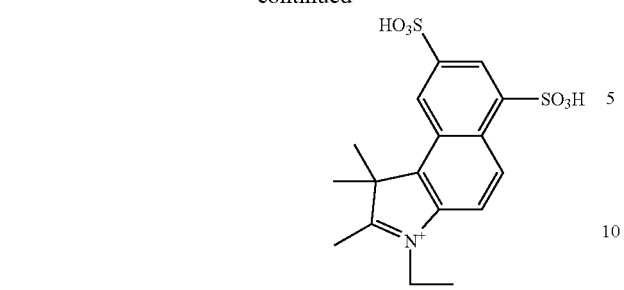
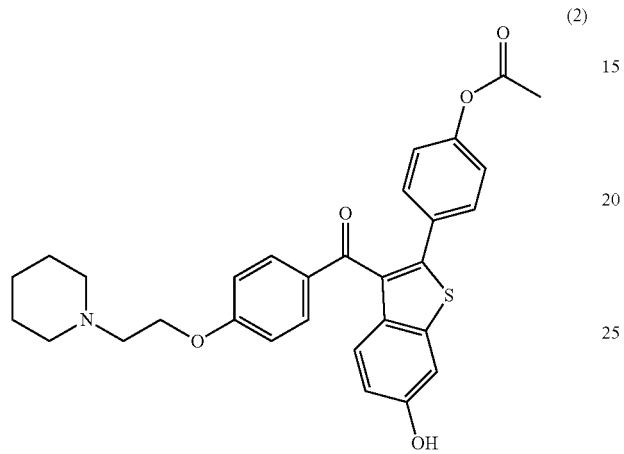
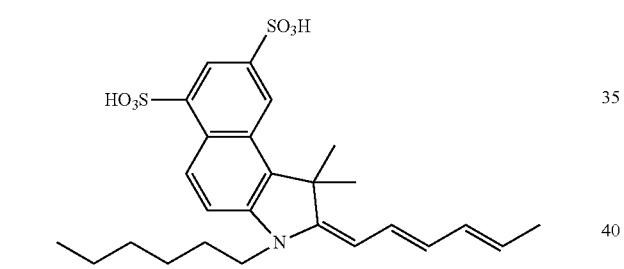
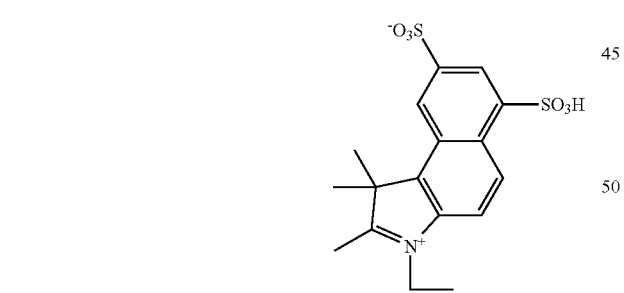
(2)
(3)
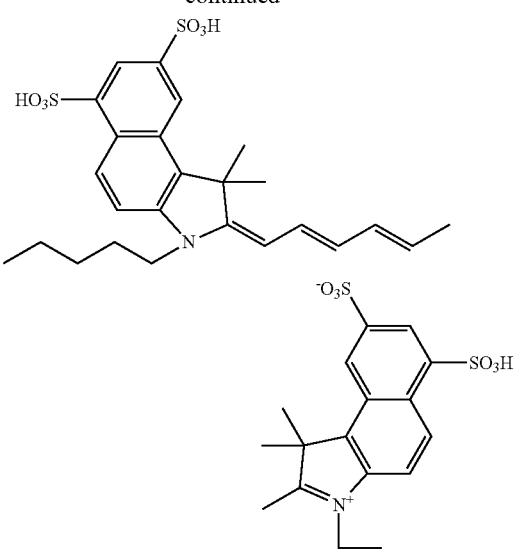
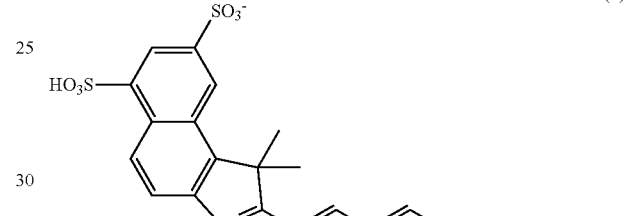
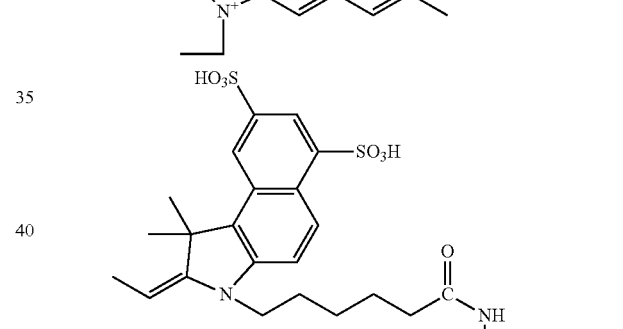
(4)
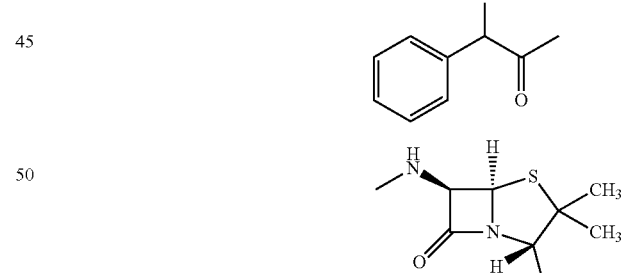
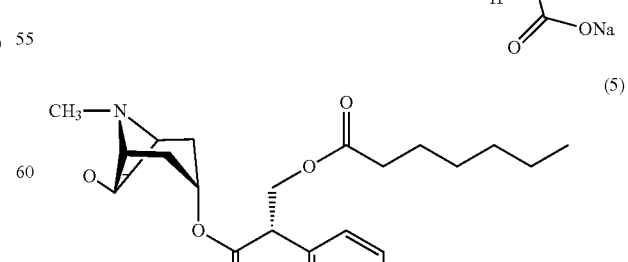
(5)

-continued

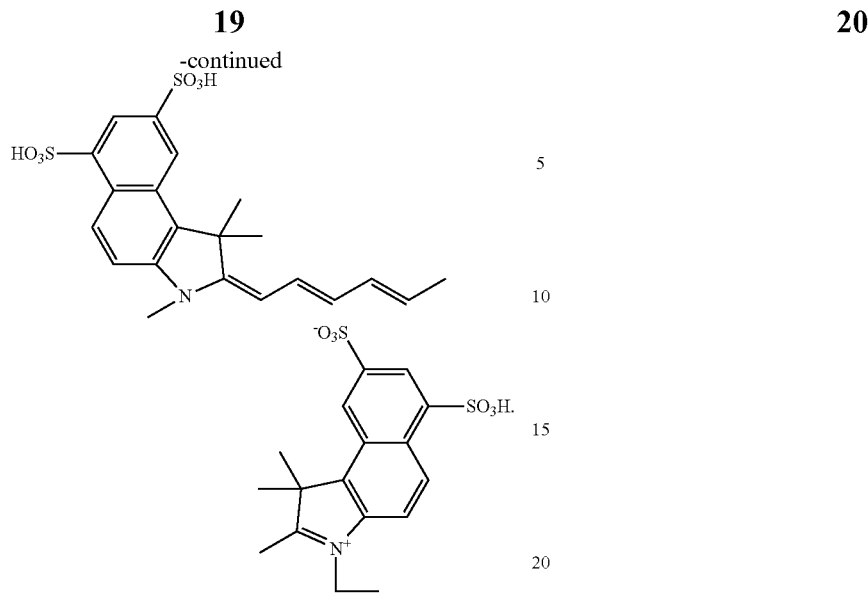

2. The drug-fluorophore complex according to claim 1, wherein the drug-fluorophore complex takes the form of a spraying dye that is sprayable onto the tumor cell site during surgery.

3. The drug-fluorophore complex according to claim 1, wherein the tumor cells are cells of at least one cancer selected from the group consisting of gastric cancer, esophageal cancer, colorectal cancer, and liver cancer.

* * * * *